US009192525B2

(12) United States Patent
Oku et al.

(10) Patent No.: US 9,192,525 B2
(45) Date of Patent: Nov. 24, 2015

(54) DISPOSABLE DIAPER

(75) Inventors: Tomomi Oku, Kagawa (JP); Satoru Sakaguchi, Kagawa (JP); Hideki Matsushima, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 571 days.

(21) Appl. No.: 13/508,608

(22) PCT Filed: Nov. 30, 2010

(86) PCT No.: PCT/JP2010/006984
§ 371 (c)(1),
(2), (4) Date: May 30, 2012

(87) PCT Pub. No.: WO2011/065026
PCT Pub. Date: Jun. 3, 2011

(65) Prior Publication Data
US 2012/0238977 A1    Sep. 20, 2012

(30) Foreign Application Priority Data

Nov. 30, 2009   (JP) ................................ 2009-272977

(51) Int. Cl.
*A61F 13/15*       (2006.01)
*A61F 13/20*       (2006.01)
*A61F 13/533*      (2006.01)

(52) U.S. Cl.
CPC .......... *A61F 13/533* (2013.01); *A61F 13/15707* (2013.01)

(58) Field of Classification Search
CPC ............ A61F 13/42; A61F 2013/8497; A61F 13/539; A61F 13/51496; A61F 2013/423
USPC ............ 604/361, 368, 380, 385.01, 385.101; 156/209, 219
See application file for complete search history.

(56) References Cited

U.S. PATENT DOCUMENTS 4,192,311 A    3/1980   Felfoldi
5,994,614 A    11/1999  Wada et al.
(Continued)

FOREIGN PATENT DOCUMENTS

GB    2452260 A    3/2009
JP    59168101 A   9/1984
(Continued)

OTHER PUBLICATIONS

International Search Report and Written Opinion for PCT/JP2010/006984 dated Mar. 8, 2011.
(Continued)

*Primary Examiner* — Jason Flick
*Assistant Examiner* — Aundria Hairell
(74) *Attorney, Agent, or Firm* — Hauptman Ham, LLP

(57) ABSTRACT

On the back sheet side, back-side recessed portions recessed toward the top sheet are provided in a surface of the absorber of the disposable diaper. The back-side recessed portions include multiple grooves, which are continuous in the longitudinal direction L of the absorber. The back-side recessed portions is visible from an outside of the back sheet in a state before the disposable diaper is used, and when the absorber absorbs liquid, the depth D of the back-side recessed portions is made smaller than that before the absorber absorbs liquid. When the hydrophilic fiber and the particulate SAP swells, and thereby the absorber expands in at least the thickness direction thereof, the back-side recessed portions seems to disappear from the outside.

20 Claims, 12 Drawing Sheets

(56) References Cited

U.S. PATENT DOCUMENTS

| | | |
|---|---|---|
| 6,838,591 B2 * | 1/2005 | Waksmundzki et al. ..... 604/382 |
| 7,479,578 B2 * | 1/2009 | Garnier et al. ................ 604/375 |
| 2003/0125682 A1 | 7/2003 | Olson et al. |
| 2003/0139717 A1 * | 7/2003 | Qin et al. ...................... 604/369 |
| 2006/0069371 A1 * | 3/2006 | Ohashi et al. ............ 604/385.01 |
| 2007/0066948 A1 * | 3/2007 | Erdman ......................... 604/380 |
| 2007/0142804 A1 * | 6/2007 | Bernard ........................ 604/375 |
| 2009/0076473 A1 * | 3/2009 | Kasai et al. ................... 604/367 |

FOREIGN PATENT DOCUMENTS

| | | |
|---|---|---|
| JP | 06190002 | 7/1994 |
| JP | 10137291 | 5/1998 |
| JP | 2001112815 | 4/2001 |
| JP | 2001112815 A | 4/2001 |
| JP | 2003144492 A | 5/2003 |
| JP | 2003190209 A | 7/2003 |
| JP | 2004222868 | 8/2004 |
| JP | 2005046263 | 2/2005 |
| JP | 2005514110 | 5/2005 |
| JP | 2006341020 | 12/2006 |
| JP | 2011030613 | 2/2011 |

OTHER PUBLICATIONS

Extended European Search Report issued Feb. 7, 2014, corresponds to European patent application No. 10832875.8.

Office Action corresponding to JP2009-272977, dated Oct. 23, 2012.

Office Action issued Jul. 11, 2014, corresponds to Egyptian patent application No. 953/2012.

Office Action issued May 8, 2014, corresponds to Philippine patent application No. 1-2012-500927.

Office Action issued May 11, 2015, corresponding to Taiwanese patent application No. 099141218.

Office Action issued Jan. 27, 2015, corresponding to Australian patent application No. 2010323996.

Office Action issued Mar. 16, 2015, corresponding to Egyptian patent application No. 953/2012.

* cited by examiner

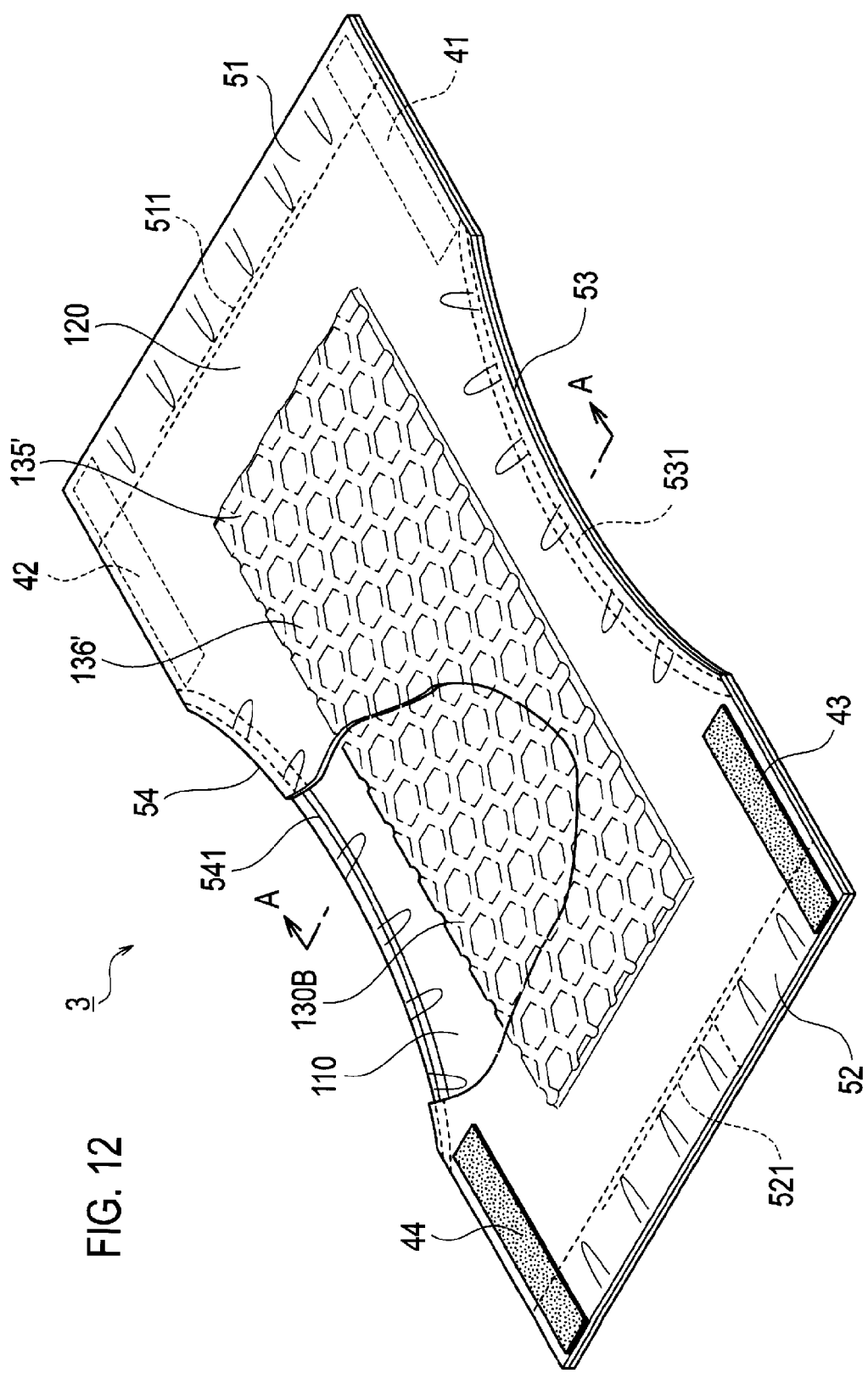

DISPOSABLE DIAPER

RELATED APPLICATIONS

The present application is a National Phase of PCT/JP10/006984, filed Nov. 30, 2010 and is based on, and claims priority from, Japanese Application Number 2009-272977, filed Nov. 30, 2009.

TECHNICAL FIELD

The present disclosure relates to a disposable diaper on which the presence or the spreading of excrement in an absorber is made visible from the outside.

BACKGROUND ART

Conventionally, there has been known a disposable diaper having an indicator visible from the outside of a back sheet to indicate the presence or the spreading of urine, excrement and the like (see Japanese Patent Application Publication No. 2006-341020 (FIG. 1, p5, and the like), for example). The indicator is a coating agent obtained by mixing a certain element with a hot melt adhesive, the element changing its color according to the hydrogen ion concentration index (PH), the hot melt adhesive joining an absorber and the liquid-impermeable back sheet to each other. The indicator is applied onto the garment side of the absorber in a predetermined region.

CITATION LIST

Patent Literature

PTL 1: Japanese Patent Application Publication No. 2006-341020

SUMMARY OF INVENTION

Technical Problem

Since the indicator is a special coating agent as described above, application thereof in a wide range increases the manufacturing cost. In addition, since the indicator is a colored coating agent, application thereof in a wide range causes an additional problem of spoiling the appearance of the disposable diaper. Specifically, when being applied in a wide range, the indicator does not match other patterns printed on the surface of an absorbent article on the garment side.

Under these circumstances, an object of one or more embodiments is to provide a disposable diaper on which the presence or the spreading of excrement in the absorber is reliably made visible from the outside, without spoiling the appearance of the disposable diaper or increasing the manufacturing cost.

Solution to Problem

To solve the above-described problem, a disposable diaper according to one or more embodiments of the present invention includes a liquid-permeable top sheet; a liquid-impermeable back sheet; and an absorber provided between the top sheet and the back sheet and configured to swell in at least a thickness direction by absorbing liquid, wherein a back-side recessed portion recessed toward a top sheet side of the absorber is formed in a surface of the absorber on a back sheet side thereof, a joint member is arranged on at least part of a surface of the back-side recessed portion, the joint member joining the back sheet to the absorber in such a manner that the back sheet follows a shape of the back-side recessed portion, the back-side recessed portion is visible from an outside of the back sheet in a state before the disposable diaper is used, and when the absorber absorbs liquid, a depth of the back-side recessed portion is made smaller than that before the absorber absorbs liquid.

One or more embodiments of the present invention can thus provide a disposable diaper on which the presence or the spreading of excrement in the absorber is reliably made visible from the outside, without spoiling the appearance of the disposable diaper or increasing the manufacturing cost.

Advantageous Effects of Invention

The present invention can provide a disposable diaper on which the presence or the spreading of excrement in the absorber is reliably made visible from the outside, without spoiling the appearance of the disposable diaper or increasing the manufacturing cost.

BRIEF DESCRIPTION OF DRAWINGS

FIG. 12 is a perspective view of a disposable diaper according to still another embodiment of the present invention, as viewed from the opposite side of the wearer's skin contact surface side.

DESCRIPTION OF EMBODIMENTS

A description is given of a disposable diaper according to the present invention with reference to the drawings. In the following description of the drawings, same or similar reference signs denote same or similar portions. In addition, it should be noted that the drawings are schematic and ratios of dimensions and the like are different from actual ones. Therefore, specific dimensions and the like should be determined in consideration of the following description. Moreover, the drawings also include portions having different dimensional relationships and ratios from each other, as a matter of course.

(Configuration of Disposable Diaper)

Figure 1:
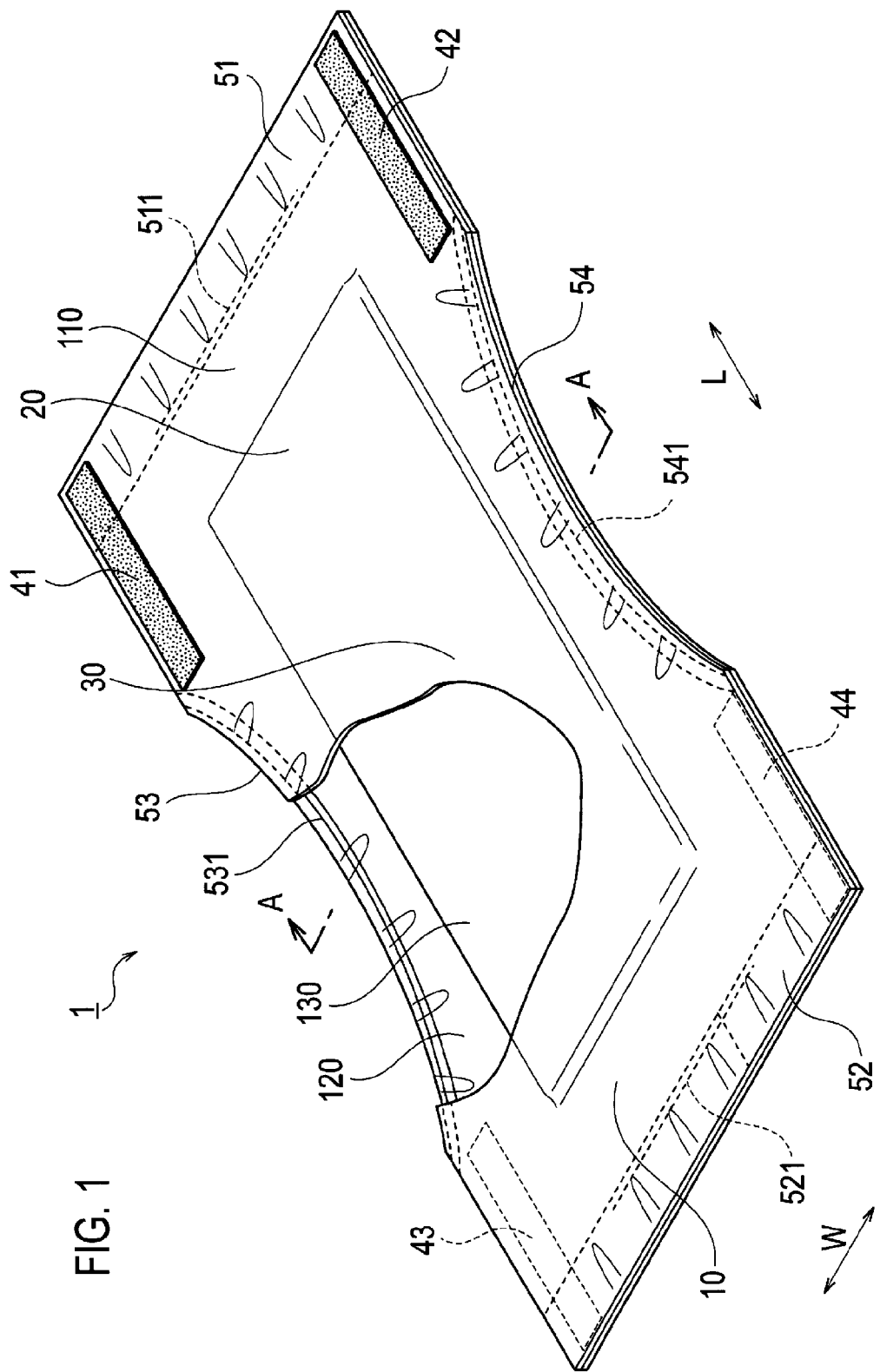
FIG. 1 is a perspective view of a disposable diaper according to an embodiment of the present invention, as viewed from the wearer's skin contact surface side.

A description is given of a configuration of a disposable diaper 1 according to an embodiment of the present invention with reference to the drawings. FIG. 1 is a perspective view of the disposable diaper 1, as viewed from the wearer's skin contact surface side.

The disposable diaper 1 includes a front waist line portion 10 for the belly side of the wearer; a back waistline portion 20 for the back side of the wearer; and a crotch portion 30 for the crotch of the wearer. The disposable diaper 1 is a so-called one-piece type diaper in which the front waistline portion 10, the back waistline portion 20 and the crotch portion 30 are integrally formed.

On the skin-contact-surface side, fastening tapes 41, 42 are respectively provided at end portions of the back waistline portion 20 in a width direction W. In addition, on an opposite side to the skin-contact surface side, fastening portions 43, 44 to which the fastening tapes 41, 42 are fastened are respectively provided at end portions of the front waistline portion 10 in the width direction W. At left and right sides of the waist of the wearer, the front waistline portion 10 and the back waistline portion 20 are joined to each other by the fastening tapes 41, 42 and the fastening portions 43, 44.

Waist gathers 51, 52 are formed in edge portions of the disposable diaper 1 in a longitudinal direction L. String-like elastic members 511, 521 are respectively arranged in the waist gathers 51, 52 in a stretched state. Leg gathers 53, 54 are formed in edge portions of the crotch portion 30 in the width direction W of the disposable diaper 1. String-like elastic members 531, 541 are arranged in the leg gathers 53, 54 in a stretched state.

The disposable diaper 1 includes a liquid-permeable top sheet 110, a liquid-impermeable back sheet 120 and an absorber 130.

Figure 2:
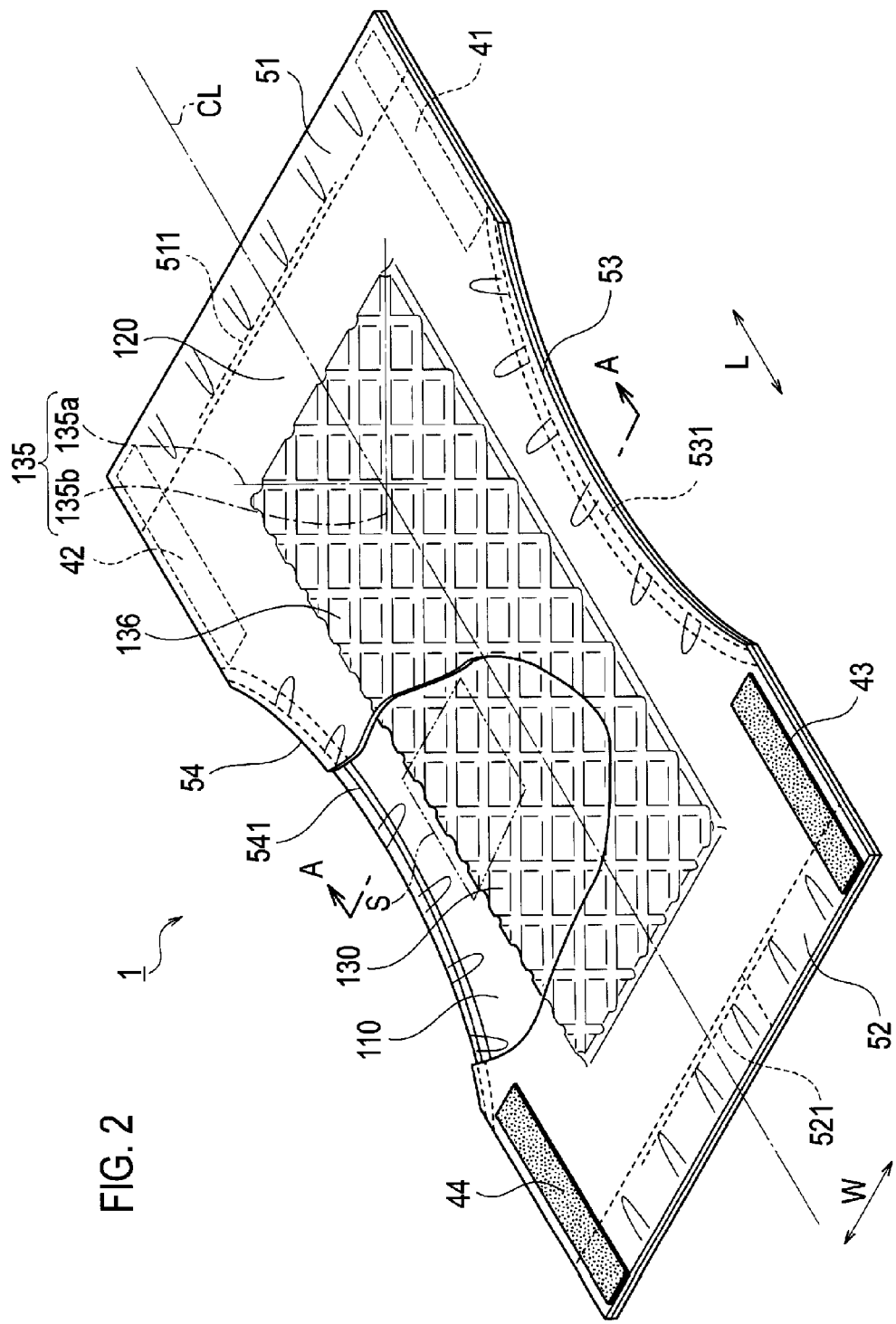
FIG. 2 is a perspective view of the disposable diaper according to the embodiment of the present invention, as viewed from the opposite side of the wearer's skin contact surface side.

FIG. 2 is a perspective view of the disposable diaper 1, as viewed from the opposite side of the wearer's skin contact surface side. As shown in FIG. 2, on the back sheet 120 side, back-side recessed portions 135 recessed toward the top sheet 110 are provided in a surface of the absorber 130 of the disposable diaper 1. The back-side recessed portions 135 include multiple grooves 135a, 135b, which are continuous. The grooves 135a are parallel to each other, and the grooves 135b are also parallel to each other.

The grooves 135a, 135b are inclined to a center line CL extending in the longitudinal direction L of the absorber 130. The grooves 135a, 135b are continuous and cross one another. The grooves 135a, 135b are inclined at an oblique angle to the center line CL. The grooves 135a may be inclined to the center line Cl at a different angle to the grooves 135b or at the same angle. The oblique angle may be between 30 and 45 degrees. As described above, the back-side recessed portions 135 form a lattice pattern in a plan view of the back sheet 120.

Figure 3:
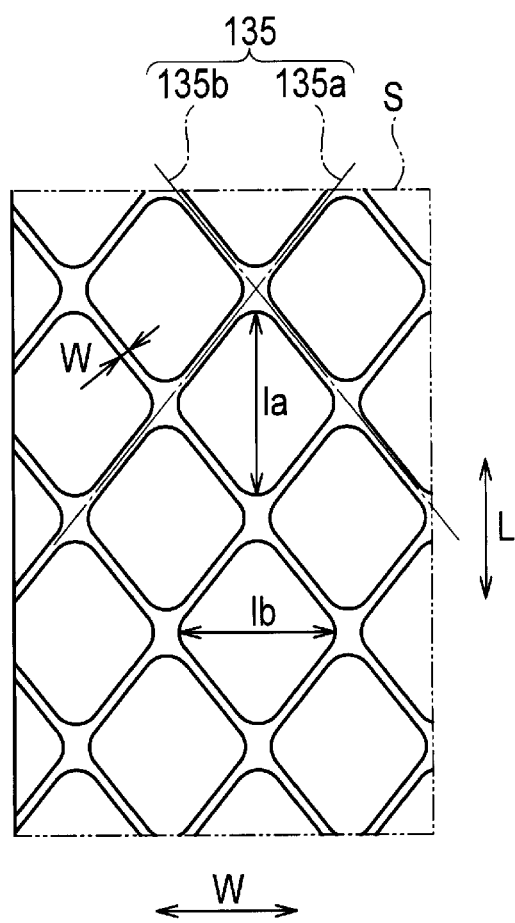
FIG. 3 is an enlarged view of a region S shown in FIG. 1.

FIG. 3 is a view obtained by enlarging a region S in FIG. 2. As shown in FIG. 3, the grooves 135a, 135b cross one another to form a lattice pattern in this embodiment. Each window portion 136, corresponding to a window of the lattice that is bounded by an adjacent pair of grooves 135a and an adjacent pair of grooves 135b, has a diamond shape in a plan view of the back sheet 120. In this embodiment, lines 1a, 1b of the diamond, which represent the height and width of the diamond, substantially correspond to the longitudinal direction L and the width direction W of the disposable diaper 1, respectively, and the line 1a is longer than the line 1b. The vertex of each window portion 136 having the diamond shape is formed into an arc shape. For example, dimensions are set as follows: a width w of each groove=1.0 mm; 1a=21 mm; and 1b=18 mm.

Figure 4:
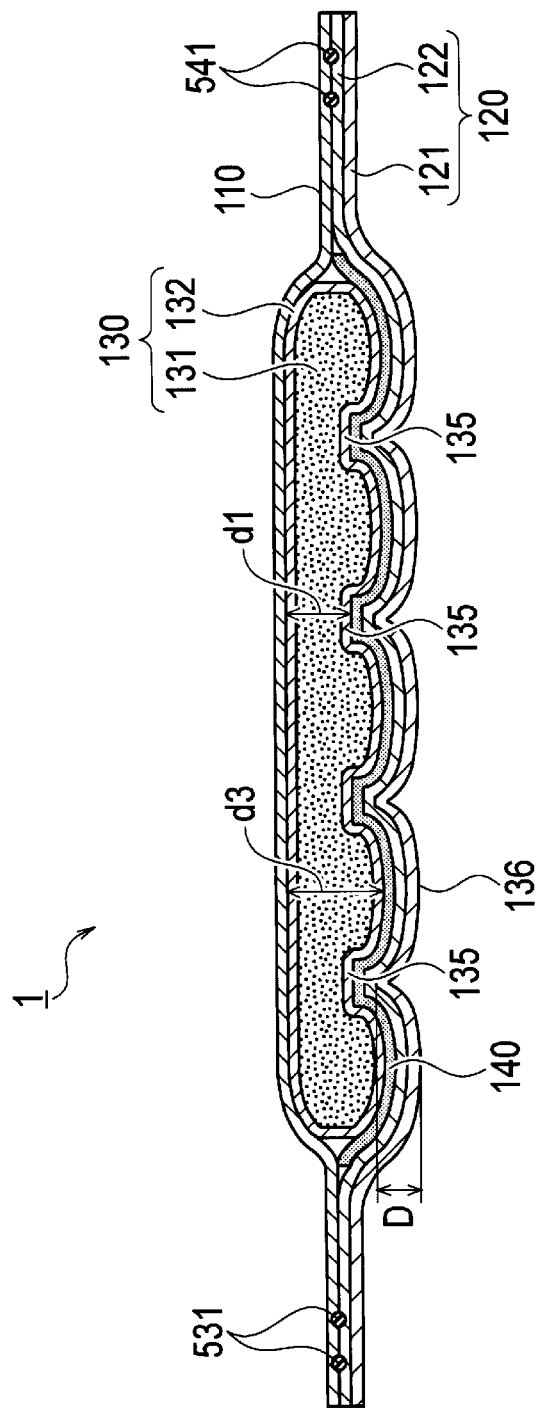
FIG. 4 is a cross-sectional view taken along the A-A line in FIG. 1.

FIG. 4 is a cross-sectional view taken along the A-A line in FIG. 1. The top sheet 110 is not particularly limited, as long as it is a sheet material having a liquid-permeable structure, such as a nonwoven fabric, a woven fabric, a porous plastic sheet, a mesh sheet, or the like. Any of natural fiber and chemical fiber may be used as a material of the woven fabric or the nonwoven fabric.

As an example of the natural fiber, cellulose such as comminute wood pulp or cotton can be cited. In addition, examples of the chemical fiber include regenerated cellulose such as rayon and fibril rayon, semisynthetic cellulose such as acetate and triacetate, thermoplastic hydrophobic chemical fiber, and hydrophilic-treated thermoplastic hydrophobic chemical fiber. Moreover, examples of the thermoplastic hydrophobic chemical fiber include single fiber such as polyethylene (PE), polypropylene (PP), polyethylene telephthalate (PET), graft-polymerized fiber of PE and PP, and compound fiber of a sheath-core structure or the like.

As a method of forming a nonwoven fabric, either a dry method (a carding method, a spunbond method, a meltblown method, an air-laid method or the like) or a wet method may be used. Multiple methods among the dry or wet methods may be combined. In addition, examples of the methods include thermal bonding, needle punching, chemical bonding and the like. The method of forming the nonwoven fabric is not limited to the above methods.

As shown in FIG. 4, the back sheet 120 includes a back nonwoven fabric 121 and a liquid-impermeable back film 122. The back nonwoven fabric 121 comes into contact with the garment, while the liquid-impermeable back film 122 is located closer to the wearer's skin than the back nonwoven fabric 121 is. The back nonwoven fabric 121 is a hydrophobic nonwoven fabric, which is formed of an SMS, a spunbond or a point-bond nonwoven fabric. The back film 122 is formed of a moisture-permeable or moisture-impermeable film. The back nonwoven fabric 121 and the back film 122 are joined to each other with a hot melt adhesive (HMA) or the like which is not illustrated. The stiffness of the back sheet 120 measured by Cantilever Method (A Method of JIS L-1096) is preferably not less than 30 mm but not more than 110 mm.

The absorber 130 is arranged between the top sheet 110 and the back sheet 120. The absorber 130 absorbs liquid such as urine and excrement of the wearer, and thus swells in at least a thickness direction. The absorber 130 has an absorbent core 131 which absorbs liquid, and an absorbent sheet 132.

The absorbent core 131 includes hydrophilic fiber and a particulate polymer absorber (hereinafter, referred to as a super absorbent polymer (SAP)). As an example of the hydrophilic fiber, cellulose such as comminuted wood pulp and cotton, regenerated cellulose such as rayon and fibril rayon, and semisynthetic cellulose such as acetate and triacetate, a particulate polymer, a fibrous polymer, thermoplastic hydrophobic chemical fiber, hydrophilic-treated thermoplastic hydrophobic chemical fiber or the like may be used alone or as a mixture thereof. Considering the cost and ease of absorbent molding, it is preferable to use the comminuted wood pulp. Hydrophilic fiber mixed with SAP may also be used. The absorbent core 131 is encapsulated with the absorbent sheet 132 such as tissue capable of absorbing liquid.

The basis weight of the absorber 130 is preferably not less than 150 g/m$^2$ but not more than 320 g/m$^2$. If the basis weight of the absorber 130 is less than 320 g/m$^2$, when forming the later-described back-side recessed portions 135 in the absorber 130, it can be ensured that the back-side recessed portions 135 are formed deeply enough to be recognized in shape through the back sheet 120. In addition, the compounding ratio of the SAP to the hydrophilic fiber is preferably 30% to 70%. The SAP compound ratio of 30% or more ensures that formation of the back-side recessed portions 135 is not suppressed and that the back-side recessed portions 135 retain their shape thereof. Moreover, the SAP compound ratio of less than 70% ensures that the back-side recessed portions 135 may follow the movement of the wearer, thus ensuring a marked discomfort in wearing is avoided. In addition, these amounts of SAP ensure that the absorbent sheet 132 is not easily torn.

The absorber 130 absorbs liquid and thereby swells in at least the thickness direction. Thus, when the absorber 130 absorbs liquid, a depth D of the back-side recessed portions 135 shown in FIG. 4 is made smaller than before the absorption of liquid by the absorber 130.

The back-side recessed portions 135 are formed in recess formation portion 137 in the absorber 130. The particulate SAP is concentrated in the recess formation portion 137.

Before the absorber 130 absorbs liquid, a thickness d1 of the absorber 130 in the back-side recessed portion 135 is preferably not less than 0.6 mm but not more than 1.3 mm, more preferably not more than 1.0 mm. When the thickness d1 of the absorber 130 is less than 1.3 mm, it can be ensured that movement of the wearer of the disposable diaper 1 does not inhibit the recessed shape of the back-side recessed portions 135 from being recognized regardless of the presence of urine. A thickness d3 of the absorber 130 in the window portion 136 is larger than the thickness d1 of the absorber 130 in the back-side recessed portion 135. The thickness d3 is preferably not less than 2.0 mm but not more than 5.0 mm, and the thickness d3 is 3.0 mm in this embodiment. In other words, the window portion 136 protrudes more from the back sheet 120 than the back-side recessed portion 135 does. A method of forming the back-side recessed portions 135 will be described in detail later.

As shown in FIG. 4, a joint member 140 is arranged on at least part of the surfaces of the back-side recessed portions 135, the joint member 140 joining the back sheet 120 to the absorber 130 to follow a shape of the back-side recessed portions 135. Accordingly, the back sheet 120 is joined to the absorber 130 to follow the shape of the surfaces of the back-side recessed portions 135 with the joint member 140. The joint member 140 may be arranged on at least part of the surfaces of the back-side recessed portions 135.

The joint member 140 is preferably an HMA which is readily applicable in any pattern. The HMA may be formed of a styrene-based polymer, a tackifier and a plasticizer. As the styrene-based polymer, a styrene-ethylene-butylene-styrene block copolymer, a styrene-butadiene-styrene block copolymer, a styrene-isobutylene-styrene block copolymer or the like may be used. The adhesive is not limited to the above; however, it is preferable to use an HMA having pressure-sensitivity exhibited at a normal temperature, which is soft and capable of adhering by entering between fibers of the adhesion target at a normal temperature.

As examples of an application method, a curtain application, a spiral application, an ohm application and the like can be cited. The ohm application is a method in which the HMA is applied in a continuous ohm letter pattern. Among these, it is preferable to use the curtain application. For example, in the case of the curtain application, 0.8 g/m$^2$ of HMA is applied in a mist state to an entire surface of the absorber 130 on the back sheet 120 side.

Figure 5:
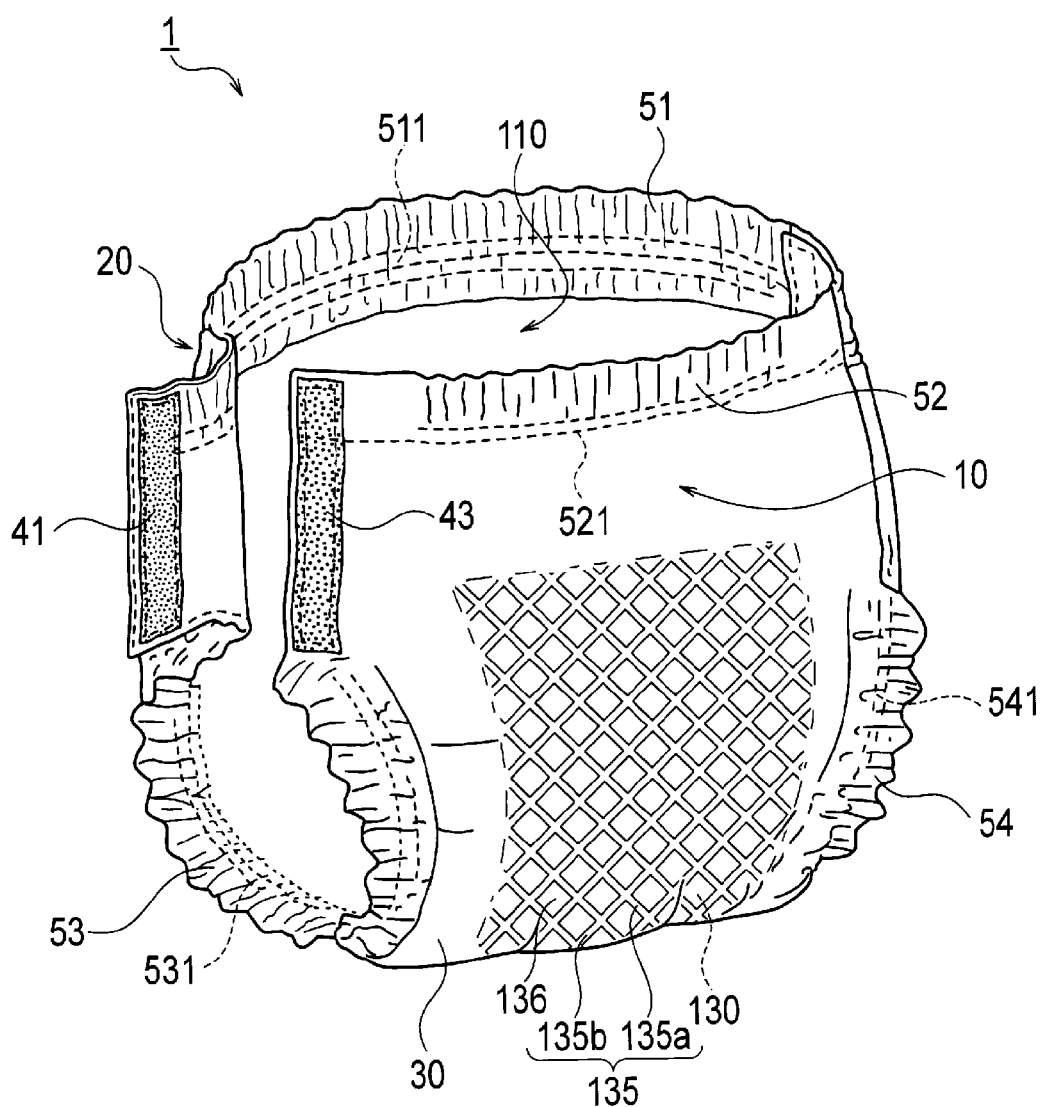
FIG. 5 is a perspective view showing the disposable diaper according to the embodiment of the present invention.

FIG. 5 is a perspective view showing a state in which the disposable diaper 1 is worn by a wearer. Note that the body of the wearer is not illustrated. As shown in FIG. 5, the back-side recessed portions 135 (grooves 135a, 135b) are formed so as to be visible from the outside of the back sheet 120 before use of the disposable diaper 1. The back-side recessed portions 135 are configured to disappear when the absorber 130 absorbs liquid.

Figure 6:
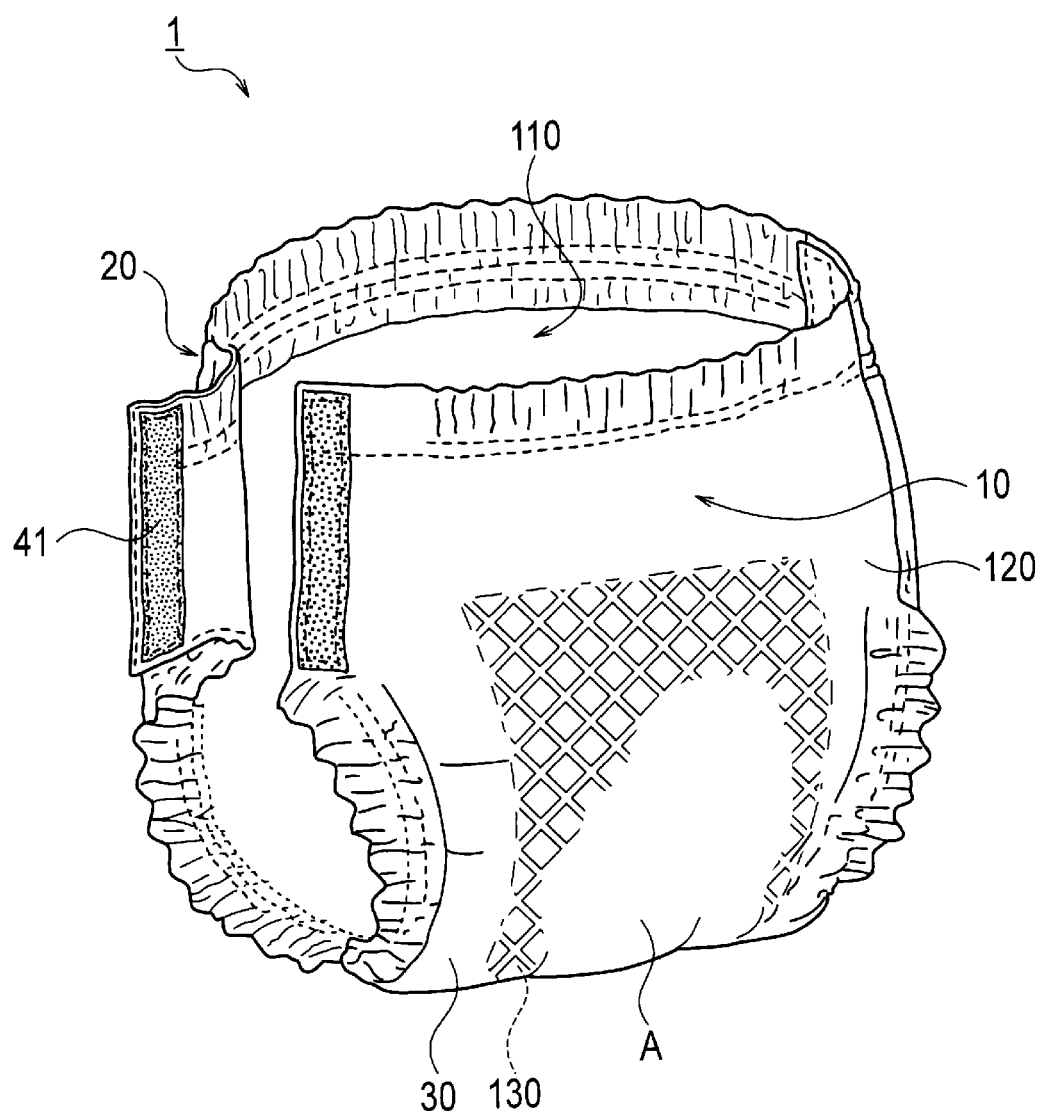
FIG. 6 is a perspective view explaining a state in which an absorber of the disposable diaper according to the embodiment of the present invention absorbs excrement.

A description is given of a state in which the absorber 130 of the disposable diaper 1 absorbs excrement (hereinafter, simply referred to as liquid) by using FIGS. 6 and 7. When the absorber 130 absorbs liquid in a region A shown in FIG. 6, the hydrophilic fiber and the particulate SAP swells, and thereby the absorber 130 expands in at least the thickness direction thereof.

Figure 7:
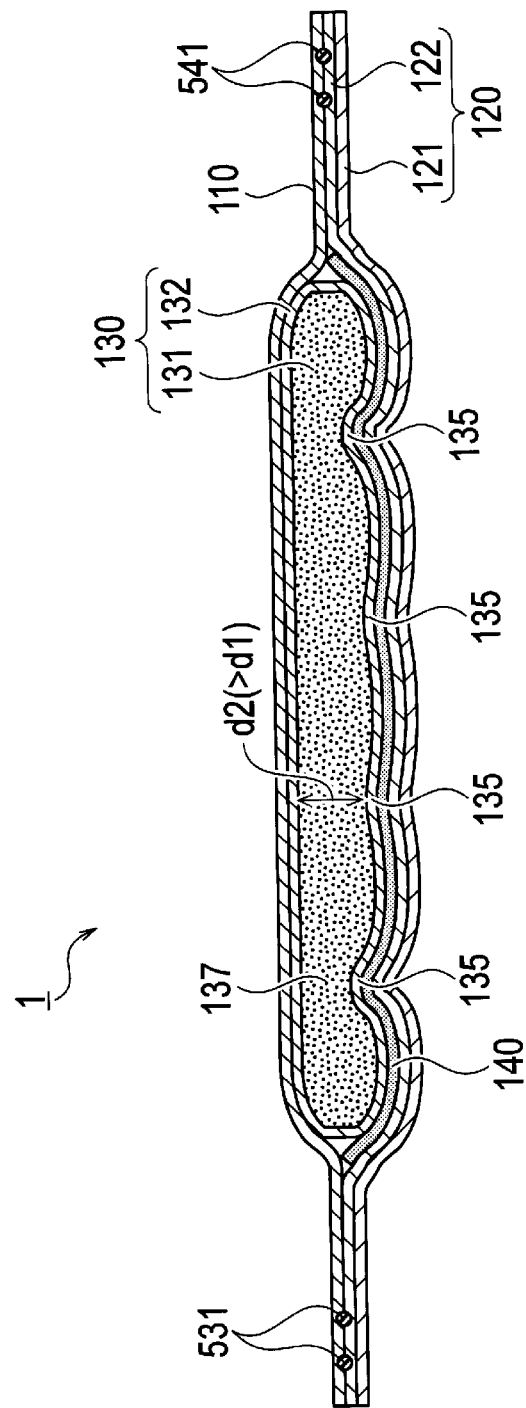
FIG. 7 is a cross-sectional view explaining the state in which the absorber of the disposable diaper according to the embodiment of the present invention absorbs excrement.

For this reason, in the recess formation portion 137 where the grooves 135a, 135b are formed, a thickness d2 of the absorber 130 after the absorption of liquid becomes larger than the thickness d1 before the absorption of liquid (see FIG. 7, d2>d1). In the region A shown in FIG. 6, the thickness d2 of the absorber 130 in the back-side recessed portions 135 is larger than the thickness d1. As a result, the depth D (see FIG. 4) of the back-side recessed portions 135 (grooves 135a, 135b) becomes smaller than before the absorption of liquid. This reduces the difference between the thickness of the absorber 130 in the grooves 135a, 135b and the thickness thereof in the window portions 136, thus making the grooves 135a, 135b less distinguishable on the back sheet 120 side than in the state before use. When the absorber 130 fully absorbs liquid, the grooves 135a, 135b disappear.

As described above, the back-side recessed portions 135 (grooves 135a, 135b) recessed toward the top sheet 110 are formed in the surface of the absorber 130 of the disposable diaper 1 on the back sheet 120 side thereof. In addition, the back sheet 120 is joined to the absorber 130 to follow the shape of the surfaces of the back-side recessed portions 135 with the joint member 140.

The grooves 135a, 135b are visible from the outside of the back sheet 120 in the state before use of the disposable diaper 1. Meanwhile, the absorber 130 absorbs liquid and thus the depth D of the grooves 135a, 135b become smaller than before the absorber 130 absorbs liquid. This eliminates the difference between the thickness of the absorber 130 in the grooves 135a, 135b and the thickness thereof in the window portions 136, making the grooves 135a, 135b less distinguishable on the back sheet 120 side than in the state before use.

For this reason, it is possible to recognize, from the outside, that the absorber 130 absorbs liquid such as urine or excrement and how largely the excrement spreads. That is, the back-side recessed portions 135 can function as a so-called indicator in the disposable diaper 1.

In addition, since the back-side recessed portions 135 are not colored, the portions do not interfere with any other pattern, and accordingly do not spoil the appearance of the disposable diaper 1. Besides, the back-side recessed portions 135 do not use a coating agent having a discoloring element depending on the hydrogen ion concentration index (PH) mixed therein, which leads to lower manufacturing cost.

The back-side recessed portions 135 are continuous. Since the back-side recessed portions 135 are formed in a lattice pattern as viewed in a plan view of the back sheet 120 particularly in the embodiment, liquid such as urine and excrement readily diffuses along the back-side recessed portions 135. When the wearer passes even a small amount of urine, the back-side recessed portions 135 become less distinguishable in a wide range and thus can reliably exert the role as the indicator.

The absorber 130 includes pulp and the particulate SAP, and the compounding ratio of the SAP to the pulp is 30% to 70%. In addition, the particulate SAP is concentrated in the recess formation portion 137. For example, when the back-side recessed portions 135 are formed by embossing, the SAP is deformed due to an applied pressure and takes in hydrophilic fiber existing around the SAP, and consequently becomes likely to tangle with the hydrophilic fiber. This suppresses separation between the SAP and the hydrophilic fiber in the recess formation portion 137, and helps retention of the shape recessed toward the inside of the absorber 130.

Accordingly, it is possible to emphasize the difference between shapes of the back-side recessed portions 135 before and after the absorption of liquid, and thus possible to reliably recognize the presence or the spreading of excrement from the outside.

In the embodiment, the basis weight of the absorber 130 is preferably not less than 150 g/m$^2$ but not more than 320 g/m$^2$. Thereby, it is possible to ensure the formation of recesses deep enough to enable recognition of the shape of the back-side recessed portions 135 through the back sheet 120.

In the disposable diaper 1, the stiffness of the back sheet 120 measured by Cantilever Method is not less than 30 mm but not more than 110 mm. This helps the back sheet 120 fit to the shape of the back-side recessed portions 135, and thus the shape of the back-side recessed portions 135 are made more visible from the outside of the back sheet 120.

The back-side recessed portions 135 are preferably formed by compressing such as embossing. The shape of the recesses of the back-side recessed portions 135 in the state before use of the disposable diaper 1 is made more visible when the back-side recessed portions 135 in the absorber 130 is formed by embossing.

(Method of Forming Back-side Recessed Portions in Absorber)

Figure 8:
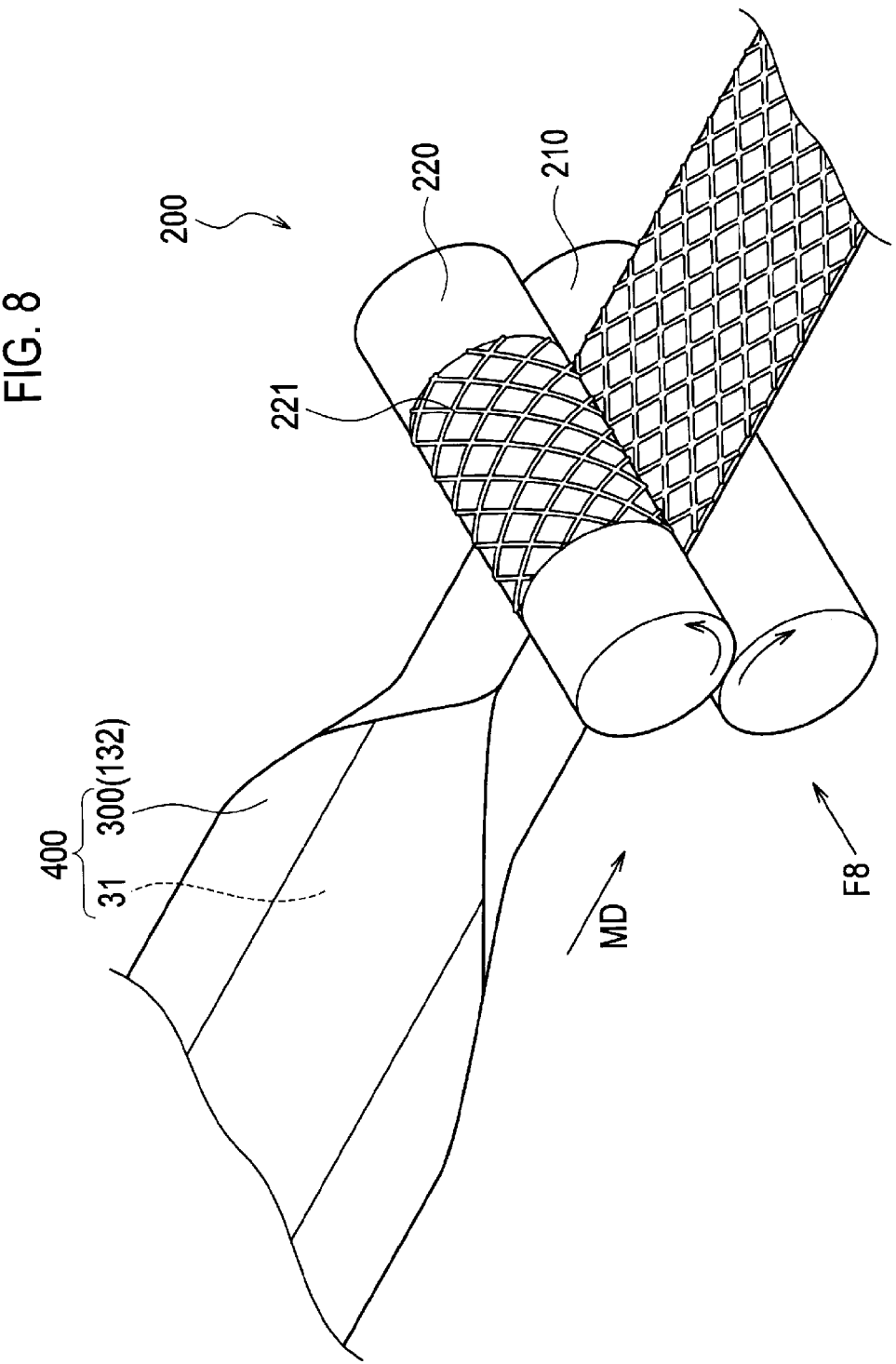
FIG. 8 is a view explaining part of a method of manufacturing the disposable diaper according to the embodiment of the present invention.

Next, a description is given of a method of forming the back-side recessed portions 135 in the absorber 130 of the disposable diaper 1. FIG. 8 is a schematic view explaining part of an apparatus for manufacturing the disposable diaper 1. An apparatus 200 has a first roll 210 and a second roll 220.

The first roll 210 rotates in a machine direction MD which corresponds to a direction of a manufacturing process flow of the disposable diaper 1, while coming in contact with an intermediate continuum 400. The intermediate continuum 400 is formed, for example, by encapsulating the absorbent core 131 in a continuum 300 of the absorbent sheets 132 forming the absorber 130. The first roll 210 is pressed against the second roll 220 to be described later with the intermediate continuum 400 placed in between.

The second roll 220 is provided with raised portions 221 on its surface, which protrude in a normal direction of the second roll 220. The raised portions 221 are formed in a lattice pattern corresponding to the shapes of the back-side recessed portions 135.

The intermediate continuum 400 passes between the two rollers of the first roll 210 and the second roll 220 which are arranged with a predetermined clearance therebetween. Thereby, the surface of the absorber 130 on the back sheet 120 side is compressed toward the top sheet 110 by the raised portions 221.

Figure 9:
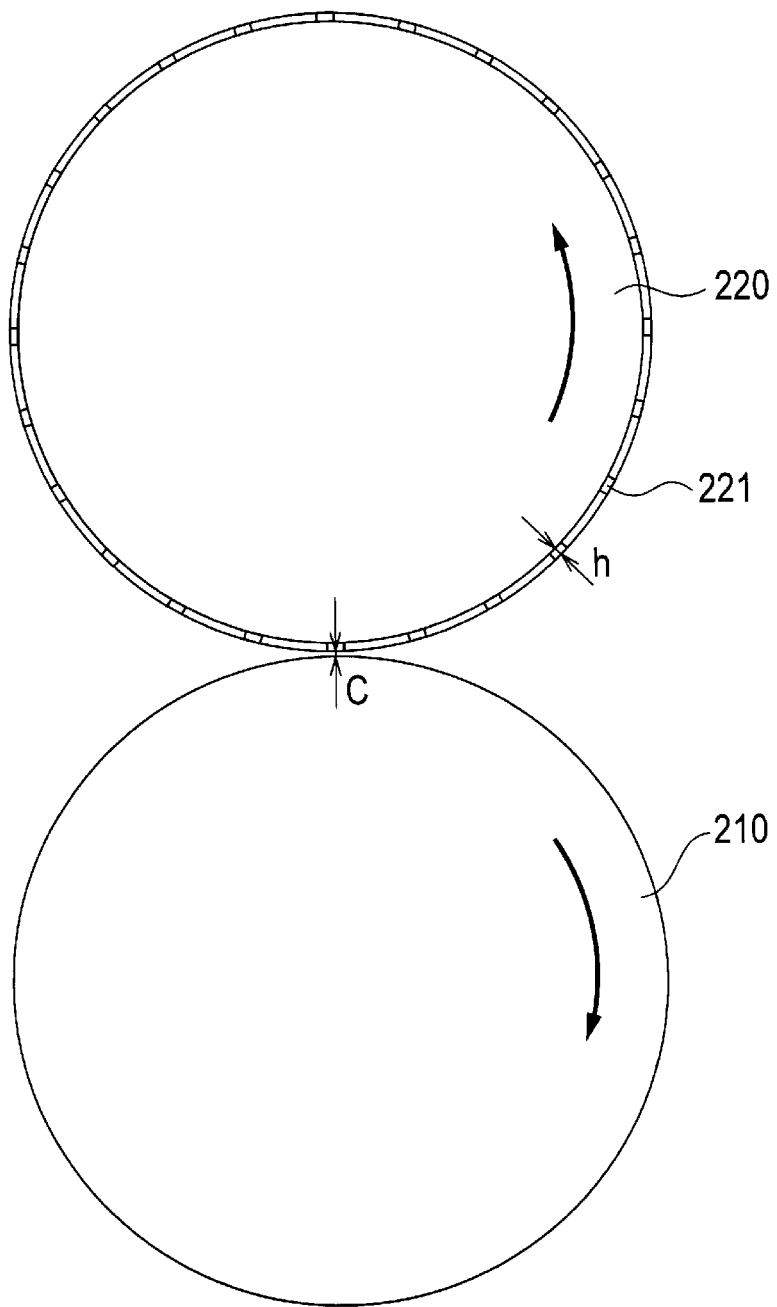
FIG. 9 is a side view of a first roll and a second roll viewed from an arrow F8 direction in FIG. 8.

FIG. 9 is a side view of the first roll 210 and the second roll 220, as viewed from a direction of an arrow F8 in FIG. 8. Note that FIG. 9 does not show the intermediate continuum 400. A clearance C between the first roll 210 and tip ends of the raised portions 221 of the second roll 220 is preferably 0.15 mm to 0.6 mm. The clearance C of at least 0.15 mm ensures that the intermediate continuum 400 may pass between the two rolls. The clearance C of 0.6 mm or less ensures that the absorber 130 is held satisfactorily, thus ensuring formation of back-side recessed portions 135 in the absorber 130 having a thickness of 1.3 mm or less.

Meanwhile, a pressure of pressing the intermediate continuum 400 by the first roll 210 and the second roll 220 is preferably 1.6 MPa to 6.3 MPa. A pressure of 1.6 MPa or more ensures retention of the shape of the back-side recessed portions 135 in the state before the absorption of liquid. A pressure lower than 6.3 MPa ensures that the back-side recessed portions 135 are not too hard, avoiding discomfort in wearing.

A protrusion height h of the raised portions 221 from the surface of the second roll 220 is preferably 0.3 mm to 2.5 mm. The protrusion height h of 0.3 mm or more ensures a difference in height between the back-side recessed portions 135 and the diamond portions corresponding to the windows, and thus the back-side recessed portions 135 are easily recognized from the outside of the back sheet 120. The protrusion height h of 2.5 mm or less reduces the possibility of a breakage of the raised portions 221 and a malfunction of the manufacturing apparatus.

(Another Embodiment 1 of Disposable Diaper)

Figure 10:
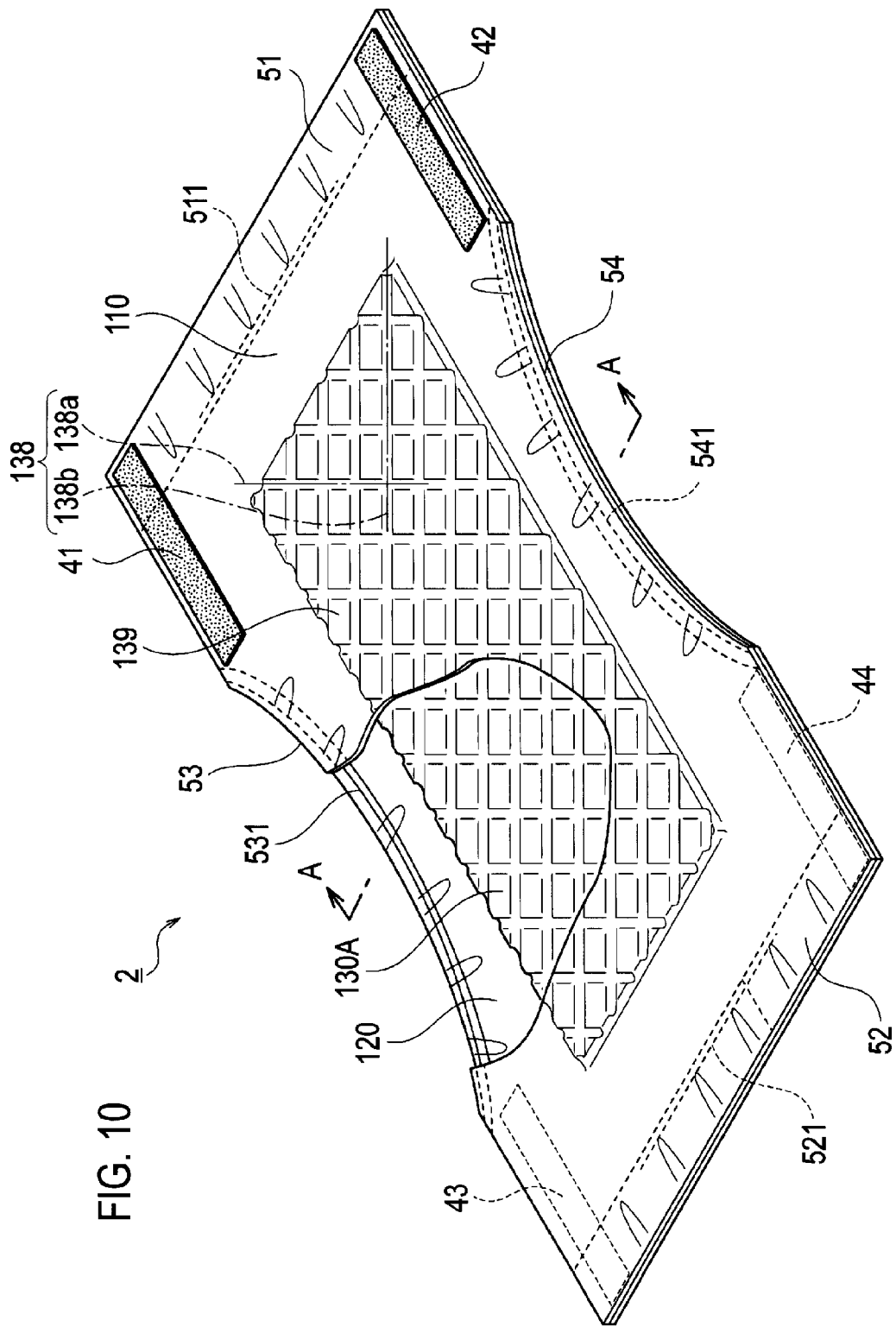
FIG. 10 is a perspective view of a disposable diaper according to another embodiment of the present invention, as viewed from the wearer's skin contact surface side.

FIG. 10 is a perspective view of a disposable diaper 2 according to another embodiment of the present invention, as viewed from the wearer's skin contact surface side. In the following description, the same reference signs denote the components having the same effects as in the disposable diaper 1 shown in FIG. 1, and the detailed description thereof is omitted.

In the disposable diaper 2, the same grooves as those formed on a back sheet 120 side of an absorber 130A may be formed in a surface on a top sheet 110 side thereof. In the disposable diaper 2, top-side recessed portions 138 recessed toward the back sheet 120 are formed in the absorber 130A on the top sheet 110 side. The top-side recessed portions 138 include multiple grooves 138a, 138b which are continuous. The grooves 138a are parallel to each other, and the grooves 138b are also parallel to each other. The grooves 138a, 138b cross one another in a plan view of the top sheet 110 and are formed in a lattice pattern. The window portions 139 corresponding to windows of the lattice each has a diamond shape.

Figure 11:
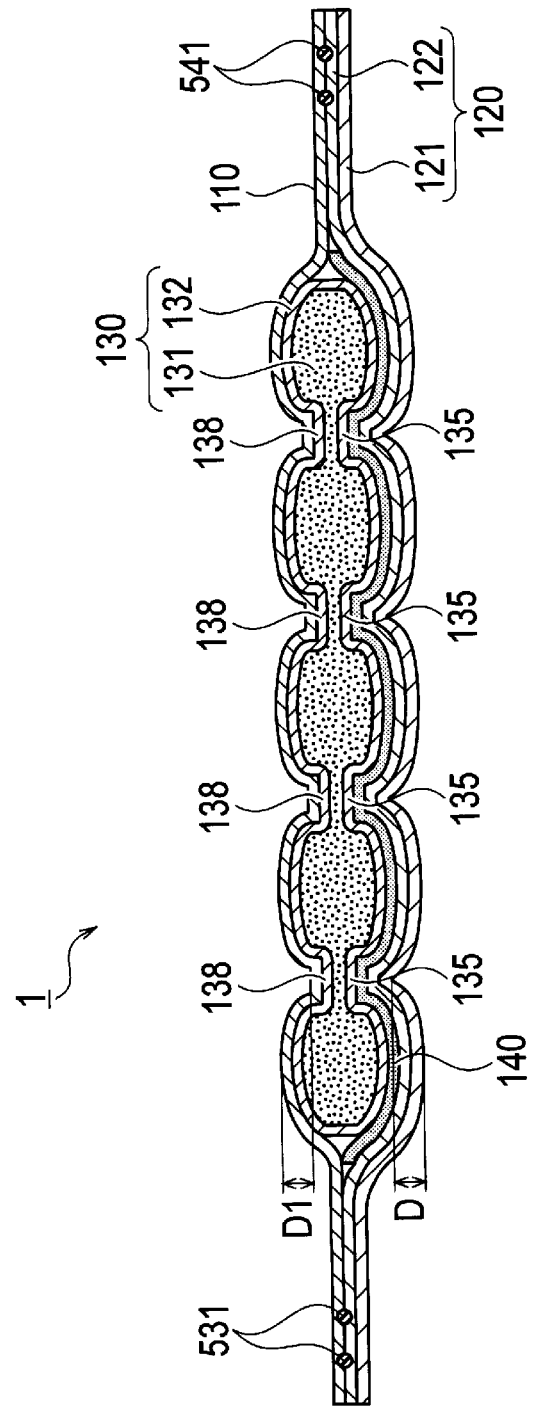
FIG. 11 is a cross-sectional view taken along the A-A line of the disposable diaper shown in FIG. 10.

FIG. 11 is a cross-sectional view taken along the A-A line of the disposable diaper 2 shown in FIG. 10. In the embodiment, the top-side recessed portions 138 are formed at positions opposed to the back-side recessed portions 135. A depth D1 of the top-side recessed portions 138 is equal to or larger than the depth D of the back-side recessed portions 135.

The top-side recessed portions 138 may be formed by using the aforementioned first roll 210 and the second roll 220 for forming the back-side recessed portions 135. For example, embossing is performed by setting the clearance C between the first roll 210 and the raised portions 221 of the second roll 220 shown in FIG. 9 in a range from 0.15 mm to 0.4 mm. In this case, recessed portions can be formed on both front and back sides of the absorber 130A even though the first roll 210 has a flat surface.

As described above, formation of the grooves in the absorber 130A on the top sheet 110 side helps liquid to diffuse over the entire absorption surface of the absorber 130A. This can prevent the lowering of the absorption amount due to an absorption saturation locally occurring in the absorber 130A. In addition, since excrement is widely diffused along the grooves, the embossed pattern disappears in a wide range even with a small amount of excrement, and thus the role as the indicator can be exerted reliably.

In addition, when the depth D1 of the top-side recessed portions 138 is larger than the depth D of the back-side recessed portions 135, liquid is more likely to be absorbed in the thickness direction of the absorber 130A from the top-side recessed portions 138 toward the back-side recessed portions 135. This accelerates an effect that the back-side recessed portions 135 become less distinguishable from the back sheet 120 side.

(Still Another Embodiment 2 of Disposable Diaper)

In the description of the disposable diaper 1, the back-side recessed portions 135 each have a diamond shape in the plan view seen from the back side. However, the shape of the back-side recessed portions 135 is not limited to the diamond. FIG. 12 is a plan view of a disposable diaper 3 according to still another embodiment of the present invention, as viewed from the opposite side from the wearer's skin contact surface side. In the disposable diaper 3, back-side recessed portions 135' are formed in a surface of an absorber 130B on the back sheet 120 side. The back-side recessed portions 135' have a honeycomb shape. Window portions 136' surrounded by the back-side recessed portions 135' protrude toward the back sheet 120.

In the disposable diaper 3, the back-side recessed portions 135' are formed into the honeycomb shape. For example, when a force is applied to the absorber 130B directing from the outside toward the center in the width direction W of the disposable diaper 3 due to movement of the wearer, the force is dispersed along the honeycomb grooves, and thus is inhibited from concentrating at a certain position of the absorber 130B. This makes it easier to retain the shape of the back-side recessed portions 135' and thus it is less likely that recesses of the back-side recessed portions 135' disappear due to movement of the wearer.

Moreover, in the disposable diaper 3, the honeycomb shape of the back-side recessed portions 135' exerts an effect that the replacement timing can be suggested properly while not spoiling the appearance of the disposable diaper 3. In addition to this, the disposable diaper 3 more readily fits to the wearer's skin surface than the disposable diaper 1 does, and thus fits the wearer more comfortably.

(Evaluation Test)

Visibility, from the outside of a back sheet, of back-side recessed portions formed in a predetermined region of a surface of an absorber on the back-sheet side thereof depends on whether or not the back sheet fits to a shape of the back-side recessed portions. In this respect, the inventors of the present invention have found an index of selecting a material which is usable as the back sheet suitable for a disposable diaper.

Table 1 shows associations of types of materials forming the back sheet, stiffness of the materials, and whether or not the back-side recessed portions are visible from the outside of the back sheet. The visibility is expressed by Excellent (A), Good (B) or Bad (D). The stiffness was calculated based on an average movement distance measured by Cantilever Method (A Method of JIS-L1096) in accordance with the following formula.

Stiffness (mm)=(average movement distance on the top side+an average movement distance on the back side (mm))/2

Test pieces (25 mm×150 mm) of materials whose stiffnesses are to be obtained were prepared. Each of the test pieces was slid on a test surface at a speed of 5 mm/sec to measure a movement distance. The sliding was performed five times each in a longitudinal direction and a width direction of the test piece, and then an average was obtained for each direction. Furthermore, an average of the average value in the longitudinal direction and the average value in the width direction was obtained. The value thus obtained was evaluated as the stiffness of the material. Table 1 shows the results.

TABLE 1

| | material | | | | | |
|---|---|---|---|---|---|---|
| | Impermeable film | Impermeable film | Impermeable film + SMS (Clothlike, curtain HMA5 g/m² for jointing) | PPSB | PPSB | PPSB |
| | Basis weight | | | | | |
| | 18.5 g/m² | 29 g/m² backside | film: 18.5 g/m², SMS: 13 g/m² | 30 g/m² | 40 g/m² | 80 g/m² |
| | topside   backside | topside   backside | topside   backside | topside   backside | topside   backside | topside   backside |
| MD (n = 5) (mm) n-time Stiffness(mm) Average | 28.1   42.7    35.4 | 26.5   55.4    41.0 | 59.2   70.2    64.7 | 80.1   67.1    73.6 | 88.2   102.6    95.4 | 122.0   125.0    123.5 |
| CD (n = 5) (mm) n-time Stiffness(mm) Average | 38.5   42.2    40.3 | 33.4   57.3    45.4 | 44.3   46.4    45.4 | 58.5   56.3    57.4 | 82.2   71.0    76.6 | 99.5   98.9    99.2 |
| MD · CD Average Stiffness | 37.9 | 43.2 | 55.0 | 65.5 | 86.0 | 111.4 |
| recessed portion Visibility from the outside of the backsheet | A | A | A | A | B | D |

The results in Table 1 show that, in order to make visible the back-side recessed portions formed in the surface of the absorber on the back sheet side, the stiffness of the top sheet is preferably not less than 30 mm but not more than 110 mm. A stiffness in the above range makes it easier for the back sheet to follow the shape of the back-side recessed portions formed in the absorber, thus enhancing the visibility of the back-side recessed portions from the outside of the back sheet. As an example of a favorable material as the back sheet is, a material obtained by joining (curtain application) 18.5 g/m² of an impermeable film and 13 g/m² of SMS nonwoven fabric with 5 g/m² of an HMA.

(Other Embodiment)

As described above, the details of the present invention have been disclosed by using the embodiments of the present invention. However, it should not be understood that the description and drawings which constitute part of this disclosure limit the present invention. From this disclosure, various alternative embodiments, examples, and operation techniques will be easily found by those skilled in the art.

The disposable diaper 1 may be a so-called three-piece type diaper formed by combining the front waistline portion, the back waistline portion and the crotch portion. The disposable diaper 1 may also be a pants-type diaper in which the fastening tape portions in the disposable diaper in the embodiments are joined in advance.

In the embodiments, the descriptions have been given of the back-side recessed portions (grooves) being continuous. What is preferred for the back-side recessed portions (grooves) is a continuous shape and having a high diffusiveness. The shape of the back-side recessed portions (grooves) is not limited to the diamond or the honeycomb. Considering the diffusiveness of liquid, it is preferable that the grooves be continuous; however, dots which have, for example, a circular shape, a rectangular shape or the like and which are discontinuous in may be provided instead. Besides, a pattern, a design or the like may be formed by the grooves.

For example, by changing the depth of the back-side recessed portions (grooves) or the formation range thereof according to the basis weight of the absorber 130, indicator functions respectively suitable for diapers having different absorption amounts can easily be given to the diapers such as a diaper for adults and a diaper for children, for example.

In the description of the embodiment, the back-side recessed portions (grooves) are formed in the substantially central portion of the absorber 130 on the back side thereof. However, the back-side recessed portions (grooves) may mainly be arranged, for example, around the waist gathers or leg gathers where reaching of urine or excrement is unfavorable.

In the descriptions of the embodiments, the back-side recessed portions are formed by embossing. However, the method of forming the back-side recessed portions is not limited to embossing. For example, the back-side recessed portions may be formed by a method in which the absorber is compressed in the thickness direction by blowing air onto the absorber.

In the description of another Embodiment 1 of the disposable diaper, the top-side recessed portions 138 can be formed without providing the raised portions on the surface of the roll located on the top sheet 110 side. However, the top-side recessed portions 138 can be formed by providing the raised portions on the surface of the first roll pressing the top surface and providing a plane anvil as the surface forming the back surface. Alternatively, the raised portions may be provided on both the rollers respectively facing the top and back surfaces.

In the description of still another Embodiment 2 of the disposable diaper, the back-side recessed portions 135' of the honeycomb shape are formed in the surface of the absorber 130B of the disposable diaper 3 on the back sheet 120 side. However, top-side recessed portions of the honeycomb shape may be formed on the top sheet 110 side. In addition, the shape may differ between the top-side recessed portions formed in the absorber 130B on the top sheet 110 side and the back-side recessed portions formed on the back sheet 120 side.

As described above, the present invention naturally includes various embodiments which are not described herein. Accordingly, the technical scope of the present invention should be determined only by the scope of claims regarded as appropriate based on the description.

Note that the entire contents of the Japanese Patent Application No. 2009-272977, filed on Nov. 30, 2009 are incorporated herein by reference.

The aspects of the present invention described above may be arranged in at least the following items:

A disposable diaper comprising: a liquid-permeable top sheet; a liquid-impermeable back sheet; and an absorber provided between the top sheet and the back sheet and configured to swell in at least a thickness direction by absorbing liquid, wherein a back-side recessed portion, recessed toward a top sheet side of the absorber, is formed in a surface of the absorber on a back sheet side thereof, a joint member is arranged on at least part of a surface of the back-side recessed portion, the joint member joining the back sheet to the absorber in such a manner that the back sheet follows a shape of the back-side recessed portion, such that the back-side recessed portion is visible from an outside of the back sheet in a state before the disposable diaper is used, and, when the absorber absorbs liquid, a depth of the back-side recessed portion is made smaller than before the absorber absorbs liquid.

Additionally, one or more of the following embodiments may be provided in accordance with the further aspects, which may be taken alone or in combination:

The back-side recessed portion may be arranged to disappear when the absorber absorbs liquid.

The back-side recessed portion may be continuous. The back-side recessed portion may comprise a plurality of continuous or discontinuous grooves.

The back-side recessed portion may be arranged in a lattice pattern in a plan view of the back sheet. The lattice pattern may comprise a plurality of continuous joined grooves. The lattice may comprise a plurality of discontinuous joined grooves. The grooves may be inclined at an oblique angle to the center line CL. The oblique angle may be between 30 and 45 degrees. The lattice pattern may comprise a series of connected diamonds.

The back-side recessed portion may be arranged in a honeycomb pattern. The back-side recessed portion may comprise a plurality of continuous grooves that define interconnected hexagons. The back-side recessed portion may comprise a plurality of discontinuous grooves that define interconnected hexagons.

The back-side recessed portion may extend continuously across the entire surface of the absorber. Alternatively, the back-side recessed portion may be provided only in the central portion of the absorber and/or in regions adjacent the waist gathers and/or the leg gathers.

The absorber may include pulp and a particulate polymer absorber, and a compounding ratio of the polymer absorber to the pulp is 30% to 70%.

The particulate polymer absorber may be concentrated in a recess formation portion in which the back-side recessed portion is formed.

A basis weight of the absorber is preferably not less than 150 g/m² but not more than 320 g/m².

A thickness of the absorber in the recess formation portion is preferably not less than 0.6 mm but not more than 1.3 mm.

A stiffness of the back sheet measured by a cantilever measurement method is preferably not less than 30 mm but not more than 110 mm.

A top-side recessed portion, recessed toward the back sheet side, may be formed on the top sheet side of the absorber, the top-side recessed portion may be formed at a position opposed to the back-side recessed portion, and a depth of the top-side recessed portion may be equal to or larger than the depth of the back-side recessed portion.

The top-side recessed portion is preferably identical to the rear-side recessed portion.

The joint member may comprise a substantially continuous layer of adhesive, which extends across the entire region of the absorber, on the back sheet side and/or the front sheet side, in which the recessed portion is provided.

The joint member may comprise a substantially continuous layer of adhesive, which extends across only the region in which the rear-side and/or front-side recessed portion is provided or across the entire rear-side and/or front-side surface of the absorber.

The joint member may be applied at a weight of 0.8 g/m$^2$. The top sheet may follow a shape of the top-side recessed portion. The shape of the top-side recessed portion may different from that of the back-side recessed portion.

The back-side recessed portion is free of any agent that changes color according to the hydrogen ion concentration index.

The back-side recessed portion may arranged mainly along a waist opening and leg openings of the diaper.

The back sheet may follow a shape of the back-side recessed portion so that the back-side recessed portion is visually distinguishable from an outside of the back sheet in a state before the absorber absorbs liquid, and when the absorber absorbs liquid, a depth of the back-side recessed portion may become smaller than that before the absorber absorbs liquid, whereby the back-side recessed portion may become less visually distinguishable to indicate bodily discharge.

The invention claimed is:

1. A disposable diaper, comprising:
   a liquid-permeable top sheet;
   a liquid-impermeable back sheet; and
   an absorber provided between the top sheet and the back sheet and configured to swell in at least a thickness direction by absorbing liquid,
   wherein
   a back-side recessed portion, recessed toward a top sheet side of the absorber, is formed in a surface of the absorber on a back sheet side thereof,
   a joint member is arranged on at least a part of a surface of the back-side recessed portion, the joint member joining the back sheet to the absorber in such a manner that the back sheet follows a shape of the back-side recessed portion,
   the back-side recessed portion is visible from an outside of the back sheet in a state before the disposable diaper is used,
   when the absorber absorbs liquid, a depth of the back-side recessed portion is smaller than before the absorber absorbs liquid, and
   the back-side recessed portion is continuous from one end of the absorber to the other end of the absorber in a longitudinal direction of the absorber.

2. The disposable diaper according to claim 1, wherein the back-side recessed portion is arranged to disappear when the absorber absorbs liquid.

3. The disposable diaper according to claim 1, wherein the back-side recessed portion includes a regular pattern continuously extending from said one end of the absorber to the other end of the absorber in the longitudinal direction.

4. The disposable diaper according to claim 1, wherein the back-side recessed portion is arranged in a lattice pattern in a plan view of the back sheet, the lattice pattern continuously extending from said one end of the absorber to the other end of the absorber in the longitudinal direction.

5. The disposable diaper according to claim 1, wherein the absorber includes pulp and a particulate polymer absorber, and a compounding ratio of the polymer absorber to the pulp is 30% to 70%.

6. The disposable diaper according to claim 5, wherein the particulate polymer absorber is concentrated in a recess formation portion in which the back-side recessed portion is formed.

7. The disposable diaper according to claim 6, wherein a thickness of the absorber in the recess formation portion is not less than 0.6 mm but not more than 1.3 mm.

8. The disposable diaper according to claim 1, wherein a basis weight of the absorber is not less than 150 g/m$^2$ but not more than 320 g/m$^2$.

9. The disposable diaper according to claim 1, wherein a stiffness of the back sheet as measured by a cantilever measurement method is not less than 30 mm but not more than 110 mm.

10. The disposable diaper according to claim 1, wherein
    a top-side recessed portion recessed toward the back sheet side is formed on the top sheet side of the absorber,
    the top-side recessed portion is formed at a position opposed to the back-side recessed portion, and
    a depth of the top-side recessed portion is equal to or larger than the depth of the back-side recessed portion.

11. The disposable diaper according to claim 10, wherein the top sheet follows a shape of the top-side recessed portion.

12. The disposable diaper according to any one of claims 11, wherein
    the shape of the top-side recessed portion is different from that of the back-side recessed portion.

13. The disposable diaper according to claim 1, wherein the back-side recessed portion is free of any agent that changes color according to the hydrogen ion concentration index.

14. The disposable diaper according to claim 1, wherein the back-side recessed portion is arranged along a waist opening and leg openings of the diaper.

15. A disposable diaper, comprising:
    a liquid-permeable top sheet;
    a liquid-impermeable back sheet; and
    an absorber provided between the top sheet and the back sheet and configured to swell in at least a thickness direction of the absorber when absorbing liquid,
    wherein
    a back-side recessed portion recessed toward the top sheet is formed in a garment facing side surface of the absorber on a side of the back sheet,
    the back sheet follows a shape of the back-side recessed portion so that the back-side recessed portion is visually distinguishable from an outside of the back sheet in a state before the absorber absorbs liquid,
    when the absorber absorbs liquid, a depth of the back-side recessed portion becomes smaller than that before the absorber absorbs liquid, and the back-side recessed portion becomes less visually distinguishable to indicate bodily discharge, and
    the back-side recessed portion is continuous from one end of the absorber to the other end of the absorber in a longitudinal direction of the absorber.

16. The disposable diaper according to claim 15, wherein a thickness of the absorber in the back-side recessed portion is not less than 0.6 mm but not more than 1.3 mm.

17. The disposable diaper according to claim 15, wherein a stiffness of the back sheet as measured by the Cantilever Method is not less than 30 mm but not more than 110 mm.

18. The disposable diaper according to claim 15, wherein
a top-side recessed portion recessed toward the back sheet is formed in a skin facing side surface of the absorber on a side of the top sheet,
the top sheet follows a shape of the top-side recessed portion, and
a depth of the top-side recessed portion is equal to or larger than the depth of the back-side recessed portion.

19. The disposable diaper according to claim 15, wherein the back-side recessed portion includes a regular pattern in a plan view of the back sheet, and the regular pattern continuously extends from said one end of the absorber to the other end of the absorber in the longitudinal direction.

20. The disposable diaper according to claim 19, wherein the regular pattern comprises a lattice pattern.

* * * * *